(12) United States Patent
Le Roux et al.

(10) Patent No.: US 8,211,881 B2
(45) Date of Patent: Jul. 3, 2012

(54) CHOLESTEROL-MIMETIC PYRENE PROBES

(75) Inventors: Christophe Le Roux, Toulouse (FR); André Lopez, Toulouse (FR)

(73) Assignee: Centre National de la Recherche Scientifique, Paris (FR)

( * ) Notice: Subject to any disclaimer, the term of this patent is extended or adjusted under 35 U.S.C. 154(b) by 1262 days.

(21) Appl. No.: 11/909,476

(22) PCT Filed: Mar. 23, 2006

(86) PCT No.: PCT/FR2006/000641
§ 371 (c)(1), (2), (4) Date: Oct. 17, 2007

(87) PCT Pub. No.: WO2006/100388
PCT Pub. Date: Sep. 28, 2006

(65) Prior Publication Data
US 2008/0187947 A1     Aug. 7, 2008

(30) Foreign Application Priority Data
Mar. 23, 2005   (FR) ...................................... 05 02884

(51) Int. Cl.
*A61K 31/56*   (2006.01)
*C07J 9/00*    (2006.01)

(52) U.S. Cl. .......................... 514/182; 552/555; 552/556

(58) Field of Classification Search .................. 514/182; 552/555, 556
See application file for complete search history.

(56) References Cited

PUBLICATIONS

Lagane et al: "Lateral distribution of cholesterol in membranes probed by means of a pyrene-labelled cholesterol: effects of acyl chain unsaturation" Biophysical Chemistry, North-Holland, Amsterdam, NL, vol. 95, 2002, pp. 7-22, XP002360396 ISSN: 0301-4622.
Li et al: "Effect of cholesteryl ester on the distribution of fluorescent cholesterol analogues in triacylglycerol-rich emulsions" BBA-Lipids and Lipid Metabolism, Elsevier Scince BV. Amsterdam, NL, vol. 1166, 1993, pp. 145-153, XP002360397 ISSN: 0005-2760 p. 146, colonne 1, ligne 16-41 figure 1.
Kao et al: "N-(2-Naphthyl)-23, 24-dinor-5-cholen-22-am in-3. beta.-ol, a fluorescent cholesterol analogue" Biochemistry, American Chemical Society. Easton, PA, US, vol. 17, No. 13, 1978, pp. 2689-2696, XP002360398 ISSN: 0006-2960 figure 1; compose IIA p. 2690, colonne 1, alinea 4.

*Primary Examiner* — Barbara P Badio
(74) *Attorney, Agent, or Firm* — Young & Thompson (57) ABSTRACT

The invention concerns compounds called pyrene-cholesterols, of general formula (I), wherein: X represents a $CH_2$ group or an oxygen atom and n is an integer from 2 to 10, as well as their use for implementing a method for detecting and measuring the effects of specific products on biological membranes, and a method for preparing the compounds.

19 Claims, 2 Drawing Sheets

CHOLESTEROL-MIMETIC PYRENE PROBES

The invention relates to membrane probes mimicking the physical properties of cholesterol, and the use of these probes within natural plasma membranes in order to characterize the collective lipid organization of the membrane thanks to a photophysical response.

Study of the functional organization of biological membranes is today a problem of a great interest [1]. Experimental approaches proposing advances in this field are based on cold selective extractions of membrane sub-assemblies resistant to the action of certain surfactants [2] called "rafts". The results of these experiments are open to serious criticism as the samples extracted may correspond to clusters formed during the extraction of insoluble membrane microdomains possibly belonging to different cellular membranes [3]. Thus, all correlation between function and initial composition of the membranes is impossible and no structural organization of the molecules can be generated without ambiguity by these biochemical approaches. The only certainty that they contribute is that the membranes form composite multi-molecular assemblies, having different average physical properties which induce activation specificities for the membrane protein systems that they contain. Thus, the membranes are not only barriers between the outside and inside of the cells, as thanks to lipid polymorphism and the particular role of sterols, a resurgence of interest is focused on them with the introduction, among others, of the concept of lipid "rafts" [4]; sub-assemblies of the plasma membrane which participate in modulation of the signalling functions carried out by cell surface proteins.

On model membranes, the properties of the phases rich in cholesterol or those of the phases rich in phospholipids constituted by unsaturated fatty acids are known and documented [5-8]. In brief, the "raft" zones are the lipid membrane zones that are thicker than the fluid zones of the liquid-disordered phase marked 1d or 1a. These "raft" zones correspond to the zones of "liquid ordered" lipid phase zones marked 1o, rotationally and conformationally constrained, composed of high percentages of cholesterol and lipids with saturated fat chains, and having a reduced translational mobility of a factor of 2 to 3 with respect to the lipid zones 1a. It should be noted that these lipid organization states of type 1a were until the last few years, recognized as the only ones existing among the different types of lipid organizations. This static description of the membranes must be completed by the fact that the constituents of these different "raft" and non-"raft" membrane zones are in a state of permanent exchange. This translational dynamic of the majority of the membrane constituents is one of the general characteristics of the membranes. On the basis of this data as a whole, to date, no method exists making it possible to establish for a given natural plasma membrane, the proportion of phase lo and la. Now, knowledge of these values or a quantity proportional to them would provide information on the significance of these "rafts" within a membrane: according to the cell type, these "rafts" could represent from 20 to 60% of the total surface of a plasma membrane! [9]. Moreover, it is accepted that certain functions take place specifically in "raft" zones and others reciprocally in non "raft" zones [1, 4], while membrane proteins taking part in these functions are found in both types of zones [10]. This problem regarding the functional organization of the plurimolecular mechanisms ensuring the functions essential to the life of any cell has given rise to the concept of transducisome, i.e. membrane sub-assemblies which are apparently "optimized technical platforms" where a given function is carried out. A sound knowledge of these is one of the major goals of modem cell biology.

Finally, in order to complete this biological description of the transducisome, it is necessary to add the conformational properties of the transmembrane proteins during the realization of their function. These introduce a logical link with the lipid phase properties detailed previously. In fact, conformational changes of these transmembrane proteins are observed during the realization of their function: The work of Salamon et al. on rhodopsin [11] or on the opioid receptor δ [12], demonstrates that a transmembrane protein can change its apparent thickness by 10% during bonding of an agonist, while this structural parameter is unchanged during bonding of an antagonist. This change of thickness could be correlated either to:

(i) variations by molecular sorting of the lateral distribution of the membrane constituents [13, 14] and thus grouping membrane constituents of a suitable thickness with that of the protein in a given functional conformation, in order to minimise a hydrophobic mismatch between protein and lipids, (ii) induction of a migration of this protein towards the thicker zones ("rafts") after bonding of the agonist and the G protein (in the case of the examples of Salamon et al. [11, 12] ), as this conformational change during cell signalling by these G-protein-coupled receptors (GPCRs) involves an increase in the thickness of the latter [11, 12].

In connection with this problem the inventors have in the past carried out studies on natural membranes on the opioid receptor hMOR and have shown a modulation of its functionality by the lipids (cholesterol) of the plasma membrane when it is expressed in eukaryotic cells (*Saccharomyces Cerevisiae* SC [15] or Chinese Hamster Ovary (CHO) cells [16] ). Thus, induction by the membrane composition of a "quasi self-assembly" state for this GPCR, capable of binding the G protein without the agonist bond, has been established.

The inventors have also used a commercial cholesterol-derived molecule: 1-pyrenemethyl-3β-hydroxy-22, 23-bis-nor-5-cholate (Py-CO2-Chol) and have shown [17] that this probe incorporated by construction into liposomes is capable of accounting for the lateral distribution of cholesterol [16, 17]. Moreover, it has also been shown that this probe is a sensitive indicator of the average phase state of the model membranes in which it is inserted. The extremes would be a membrane where the lipids are in a la type phase state (membrane characterized by a low thickness) on the one hand, or a membrane of which the lipid phase is a lo type (high thickness membrane) on the other hand. Thus, by static fluorescence measurements of the ratio of bands 1 and 3 of the monomer of the pyrene fluorophore, it is possible to arrive at a characterization of the average phase state [16]. This property is characteristic of the non-substituted pyrene [18]. It is not there with the pyrene phospholipids [19] and is there with the compounds of the Py-Chol family.

Nevertheless this commercial probe, Py-CO2-Chol, poses a problem regarding the possibility of marking the natural plasma membranes. Its low solubility in membrane lipids compared to that of cholesterol (7% instead of 68% in DMPC) is the reason. The bond of the ester junction between the pyrene and cholesterol groups (of a polar nature) cutting the hydrophobic parts of this compound, could be responsible for this fact [17]. The invention provides a solution to the impossibility of carrying out this type of measurement on living cells with commercial fluorescent molecules mimicking cholesterol.

Moreover, this static fluorescence approach of the compartmentation of the natural membranes has been completed by measurements of the characteristic parameters of the dynamics of the membrane constituents: SPT (Single Particle Tracking) [21-23] or FRAPrv (Fluorescence Recovery after photobleaching at variable radius) experiments [24, 25] have proved the existence of lateral dynamic structures of submicrometric size, in situ in cells. These two dynamic approaches are complementary (individual observations SPT or analysis of a collective behaviour using FRAPrv). Thus:

i) Through SPT the movements of individual hMOR receptors, on the surface of NRK cells have demonstrated an hMOR translational diffusion mode combining a confined diffusion mode superimposed on a random walk of the confinement. [21-22].

ii) In-depth statistical analysis of the results has enabled the development of an explanatory theoretical model of the confinements observed and the interactions which may generate them [21-22]. It introduces a new type of confinement without a barrier, imposed only by the interactions between the membrane entities.

iii) The transducisome concept and its development specificity as well as its surface significance on a type of cell have been demonstrated by FRAPrv on HEK cells and for the function of GPCRs with neurokine [25].

The purpose of the invention is principally to provide molecular probes which can be inserted effectively into the biological membranes of in vivo cells, in particular by means of methyl-β-cyclodextrins, and which by their response are capable of accounting for the average variations in lateral distributions of the membrane constituents.

As such, the inventors were able to synthesize novel mixed compounds from cholesterol and pyrene, having a ketone or methylene group at the junction between the cholesterol and the pyrene, with a linker arm of a variable length.

Surprisingly, the inventors have shown that not only are the compounds pyrene-ketone-cholesterol and pyrene-methylene-cholesterol excellent indicators of the average condition of the lipids by means of their fluorescence properties, but also that the propensity of these compounds for insertion into natural membranes is remarkable.

The main subject of the invention is the compounds hereafter called pyrene-cholesterol, of general formula (I):

in which X represents a CH$_2$ group or an oxygen atom and n is an integer from 2 to 10, in particular from 2 to 6.

The invention relates to more particularly to a compound of general formula (I) called pyrene-ketone-cholesterol, of the following formula (4):

More particularly, the subject of the invention is also a compound of general formula (I) called pyrene-methylene-cholesterol, of the following formula (7):

The invention also relates to the use of a pyrene-cholesterol compound of formula (I) previously defined, or a combination of these pyrene-cholesterol compounds, for the study of the functional organization of biological membranes and its changes under the effect of external stimuli such as temperature, pressure, the addition of an extrinsic agent modifying the concentration of a lipid initially contained in said biological membranes, or the addition of a given product.

By "functional organization of biological membranes" for a given biological function, is meant the characteristic lipid parameters of the structure of the membrane such as the phase state of the lipids (ordered liquid lo or disordered liquid 1d) and/or lateral distribution of the membrane constituents which participate in the optimisation of the given biological function.

Known examples of extrinsic agents capable of modulating the concentration of a given lipid of biological membranes, are the compounds of the cyclodextrin family which specifically deplete the membranes of certain lipids, or other extrinsic lipophilic agents which modulate the membrane fluidity by insertion (rigidification or fluidification). [26] More particularly, the subject of the invention is the above-mentioned use of a pyrene-cholesterol compound of formula (I) in the context of implementing a method of detection, and, if appropriate, measurement of the polarity or the permeability of biological membranes, the concentration of one or more constituents of these membranes, and thus the invention allows changes in the spatial and collective organization of the constituents of these biological membranes induced by these extrinsic factors, to be accounted for.

Examples of constituents of the membranes the presence of which can be detected or the concentration measured according to the invention are cholesterol or G-protein-coupled membrane receptors (GPCR) during triggering of their signalling by a ligand. By "spatial and collective organization of the constituents of biological membranes" is meant the type of average lipid phase representative of the membrane phase states before and after activation of GPCR by the extrinsic agent.

The invention relates more particularly to the above-mentioned use of a pyrene-cholesterol compound of formula (I) above, in the context of implementing a method of detection, and, if appropriate, of photophysical measurement of the effects of given products on biological membranes, said method being applied to:
 screening bioactive products capable of being agonists or antagonists of receptors present in cell membranes or on the surface of these membranes, said bioactive products being capable of being used for the preparation of medicaments intended for the treatment of pathologies in which said receptors are involved;
 in vitro diagnosis of pathologies from cells of patients using given products used as markers of these pathologies, in particular cells capable of being sensitive to a given product used as a marker, the effect of which on these cells is characteristic of a pathology,
 monitoring the direction of the therapeutic indication of a medicament comprising a bioactive product as defined above, by in vitro determination of the agonist or antagonist effect of this medicament on the cells of the patient capable of being treated with this medicament; advantageously, this method of monitoring makes it possible to guide the physician towards a personalized treatment as suitable as possible for a particular patient, with a bioactive product selected in this way.

Examples of bioactive products capable of being screened thanks to the invention are agonist or antagonist ligands of GPCR. The latter being previously overexpressed in the plasma membranes of the biological cells.

Examples of pathologies against which medicaments can be prepared from bioactive products screened according to the invention are all the pathologies of which the agent responsible is a membrane receptor of the GPCR family (60% of current pharmacological targets).

According to a preferred embodiment of the above-mentioned uses of a pyrene-cholesterol compound of formula (I) according to the invention, biological membranes are chosen from the group constituted by vesicles, unilamellar liposomes, multilamellar liposomes, bilayers or supported lipid multilayers, extracted cell membranes or cell membranes of living cells.

By "supported lipid multilayers" is meant model membranes corresponding to the superposition of one, two or more lipid bilayers which are high-performing membrane models for photophysical studies and measurements.

Advantageously, the above-mentioned cell membranes are those of the following eukaryotic cells: CHO (Chinese hamster ovary cell), HEK (human endothelial kidney cell), NRK (normal rat kidney cell) AEB (aortic endothelial bovine cell), AEH (aortic endothelial human cell), SHY5Y (neuroblastoma), 3T3, primary cultures of neurones, fibroblasts, or originating from other organs or tissues.

A subject of the invention is also a method for studying the functional organization of biological membranes, and implementing a method for detecting and, if appropriate, measuring the effects of external stimuli such as temperature, pressure, modulation by an extrinsic agent of the lipid concentration contained initially in said biological membranes, or the addition of a given product influencing the organization of said biological membranes, characterized in that it comprises:
 a stage of incorporation of a compound of formula (I) defined above, or a combination of several of these compounds, into said biological membranes,
 if appropriate, the application of external stimuli as defined above, to said membranes, a stage which is skipped for the reference measurements,
 the application to said biological membranes of a radiation of wavelength $\lambda_{ex}$ characteristic of the absorption of pyrene, $\lambda_{ex}$ being comprised between 330 nm and 350 nm,
 the measurement of the intensity of the fluorescence radiation emitted by said biological membranes at an emission wavelength of 375 to 385 nm, characteristic of pyrene emission band 1, this intensity being a function of the polarity of the membrane,
 the measurement of the intensity of at least one of the two fluorescence radiations emitted by said biological membranes between 390 nm and 425 nm, characteristic of pyrene emission bands 3 and 4, this intensity being a function of the quantity of pyrene, and therefore of compounds according to one of claims 1 to 3, in said membranes,
 the determination of the ratio between the intensity of band 1 and that of band 3 and/or 4, namely the ratios $I_1/I_3$ and/or $I_1/I_4$,
 the correlation between the ratio measurement during the previous stage, and the level of polarity of said membranes which is a function of their thickness, thus giving an indication of the average type of functional organization of these membranes and its development under the effect of an external stimulus.

Advantageously, the method mentioned above is applied to the screening of bioactive products capable of being agonists or antagonists of receptors present in cell membranes or partially inserted in these membranes, said bioactive products being capable of use for the preparation of medicaments intended for the treatment of pathologies in which said receptors are involved, said method comprising:
 a stage of incorporation of a compound of formula (I) defined above, or a combination of several of these compounds, into said biological membranes,
 the placing said membranes in the presence of a bioactive product, or a bank of bioactive products, under conditions allowing these products to bind with the membrane receptors,
 if appropriate, a stage of rinsing said membranes to remove any bioactive product which would not be capable of binding with a membrane receptor,
 the application to said biological membranes of a radiation of wavelength $\lambda_{ex}$ characteristic of the absorption of pyrene, $\lambda_{ex}$ being comprised between 330 nm and 350 nm,
 the measurement of the intensity of bands 1, 3, and/or 4, and the determination of the ratios $I_1/I_3$ and/or $I_1/I_4$,
 the comparison of the ratios $I_1/I_3$ and/or $I_1/I_4$, obtained in the previous stage with the ratios $I'_1/I'_3$ and/or $I'_1/I'_4$, measured in the absence of bioactive products, which allows the agonist or antagonist or inverse antagonist nature of the bioactive product or products tested to be determined, an agonist product being characterized by a ratio $I_1/I_3$ and/or $I_1/I_4$ respectively, greater than or less than the ratio $I'_1/I'_3$ and/or $I'_1/I'_4$ according to the type of said receptors, an antagonist product being characterized by a ratio $I_1/I_3$ and/or $I_1/I_4$ equivalent respectively to the ratio $I'_1/I'_3$ and/or $I'_1/I'_4$, an inverse antagonist product being characterized by a ratio $I_1/I_3$ and/or $I_1/I_4$ respectively less than or greater than the ratio $I'_1/I'_3$ and/or $I'_1/I'_4$ i.e. an inverse effect to that of an agonist product.

The invention relates more particularly to a method as defined above characterized in that it is carried out in vitro on eukaryotic cells, and comprises a stage of incorporation of a compound of formula (I) of the invention, or a combination of several of these compounds, into the membranes of these cells.

Advantageously, in the above-mentioned methods of the invention, the stage of incorporation of a compound of the invention, or the combination of several of these compounds into said membranes, is carried out using a transporter intended to exchange cholesterol, a phospholipid, naturally present in said membranes, with said pyrene-cholesterol compound or said combination.

Preferably, the methods defined above are characterized in that the transporter is a methyl-β-cyclodextrin, or an α-, β-, γ-cyclodextrin.

More particularly, a subject of the invention is a method as defined above, characterized in that the proportion of compound of formula (I) of the invention, or the combination of several of these compounds, incorporated into said membranes represents approximately 0.1 to 2% of the surface concentration of lipids present in the biological membrane.

A subject of the invention is also a composition characterized in that it comprises a compound of formula (I) of the invention, or a combination of several of these compounds, in a mixture with a transporter intended to exchange cholesterol or a phospholipid, naturally present in said membranes with said pyrene-cholesterol compound or said combination.

Preferably, this composition is characterized in that the transporter is a methyl-β-cyclodextrin, or an α-, β-, γ-cyclodextrin.

A subject of the invention is also the use of the composition defined above in the stage of incorporation of a compound of the invention, or a combination of several of these compounds, into said biological membranes, during the implementation of a method as defined above.

A subject of the invention is also a synthesis method for the compounds defined above, characterized in that it comprises the following stages:

a) reacting the pregnenolone of formula (a) and the pyrene derivative of formula (b) in which n is an integer from 2 to 10, in particular from 2 to 6, in the presence of EtOK, EtOH, in CH$_2$Cl$_2$ at a temperature comprised between 5° C. and 20° C. and for a duration comprised between 10 and 72 hours, which produces the following compound of formula (1):

b) reacting the compound of formula (1) obtained in the previous stage in the presence of 1.5 equivalents of Ac$_2$O, 10 mol % of DMAP, 1 equivalent of Et$_3$N, in CH$_2$Cl$_2$ for 3 hours, which produces the following compound of formula (2):

(2)

c) reacting the compound of formula (2) obtained in the previous stage in the presence of 2 equivalents of TiCl$_4$, 1.5 equivalents of Et$_3$SiH, in CH$_2$Cl$_2$ for 45 minutes at ambient temperature, which produces the following compound of formula (3):

(2)

(3)

d) reacting the compound of formula (3) obtained in the previous stage in the presence of MeONa, CH$_2$Cl$_2$ for 4 hours at ambient temperature, which produces the following compound of formula (4):

(3)

(4)

e) if appropriate, reacting the compound of formula (4) obtained in the previous stage in the presence of TBDMSCl, imidazole, in CH$_2$Cl$_2$ for 12 hours at ambient temperature, which produces the following compound of formula (5):

-continued (5)

f) reacting the compound of formula (5) obtained in the previous stage in the presence of 2 equivalents of CH$_2$=PPh$_3$, in a THF/DMSO mixture, for 12 hours at 75° C., which produces the following compound of formula (6):

(5)

(6)

g) reacting the compound of formula (6) obtained in the previous stage in the presence of 5 equivalents of TBAF, in THF, for 12 hours at 65° C., produces the following compound of formula (7):

(6)

(7)

EXPERIMENTAL PART

All the commercial chemical products are used in the condition in which they are received. All the reactions are carried out under argon, using the standard Schlenk method. The proton and carbon 13 NMR data are obtained with a Bruker Avance 300 device. The mass spectrograms are obtained with a NERMAG R10-10 device under chemical ionisation conditions with ammonia or methane. The infra-red spectra are obtained on a Series 1600 Perkin Elmer FTIR in the form of KBr pellets and are indicated in cm$^{-1}$. The melting points are not corrected.

Synthesis of (21E)-3β-hydroxy-pregna-5,21-diene-22-(1-pyrenyl)-20-one (compound 1)

15 mL of dry ethanol then 25 mL of a solution of potassium ethanolate at 24% by weight in ethanol are added to a solution of 1-pyrenecarboxaldehyde (3.2 g, 14 mmol) and pregnenolone (4 g, 12.64 mmol) in 30 mL of dry $CH_2Cl_2$, and the solution is stirred for 72 h at +5° C. 200 mL of water is added and the organic products are extracted with $CH_2Cl_2$ (3×100 mL). The combined organic extracts are rinsed with salt water, dried over sodium sulphate, filtered and evaporated. Purification by flash chromatography on silica G60 (0.040-0.063 mm), elution with ethyl acetate in $CH_2Cl_2$ (2/98) then with ethyl acetate in $CH_2Cl_2$ (15/85) produce 6.12 g (91%) of compound 1 in the form of a brilliant yellow solid; mp: 153° C.; TLC ($CH_2Cl_2$/AcOEt 15:85) $R_f$ 0.5; IR (KBr, cm$^{-1}$) 3300m, 2932s, 1676m, 1590s, 1436w, 1370w, 1352w, 1315w, 1234w, 1192w, 1102m, 1052m, 973w, 848s, 709w; $^1$H NMR (CDCl$_3$) δ 0.59 (s, 3H), 0.87 (s, 3H), 0.70-2.38 (m, 22H), 2.73 (t, J=8.7 Hz, 1H), 3.42 (sept, J=4.8 Hz, 1H) 3.55 (t, J=9 Hz, 2H), 5.24 (d, J=4.8 Hz, 1H), 6.87 (d, J=15.6 Hz, 1H), 7.87-8.17 (m, 8H), 8.36 (d, J=9.3 Hz, 1H), 8.58 (d, J=15.6 Hz, 1H), $^{13}$C NMR (CDCl$_3$) δ 200.2, 140.8, 138.0, 132.7, 131.3, 130.7, 130.2, 128.7, 128.6, 128.5, 127.3, 126.3, 126.0, 125.8, 125.0, 124.9, 124.6, 124.0, 122.5, 121.4, 71.7, 62.5, 57.1, 53.5, 50.0, 45.1, 42.3, 39.2, 37.3, 36.5, 32.0, 31.8, 31.6, 24.7, 22.8, 21.1, 19.4, 13.5; MS (CI, NH$_3$) m/z 529 (100, [M+H]$^+$).

Synthesis of (21E)-3β-acetoxy-pregna-5,21-diene-22-(1-pyrenyl)-20-one (compound 2).

Acetic anhydride (1 mL, 5.28 mmol), 4-(dimethylamino)pyridine (30 mg, 246 μmol) and triethylamine (343 μL, 2.46 mmol) are added successively to a solution of compound 1 (1.3 g, 2.46 mmol) in 20 mL of $CH_2Cl_2$. The solution obtained is stirred for 3 h at ambient temperature, then water (150 mL) is added and the organic products are extracted with $CH_2Cl_2$ (3×80 mL). The combined extracts are dried over sodium sulphate, concentrated under reduced pressure and after column chromatography ($CH_2Cl_2$/AcOEt 98/2) produce 1.16 g (83%) of compound 2 in the form of a yellow solid; mp 99° C.; TLC (AcOEt/$CH_2Cl_2$ 2:98) $R_f$ 0.9; IR (KBr, cm$^{-1}$) 2938s, 1728s, 1676w, 1590s, 1371m, 1242s, 1102m, 1126m, 845s; $^1$H NMR (CDCl$_3$) δ 0.58 (s, 3H), 0.87 (s, 3H), 1.95 (s, 3H), 0.70-2.36 (m, 21H), 2.71 (t, J=9 Hz, 1H), 4.52 (m, 1H), 5.24 (d, J=4.8 Hz, 1H), 6.85 (d, J=15.6 Hz, 1H), 7.87-8.17 (m, 8H), 8.36 (d, J=9.6 Hz, 1H), 8.56 (d, J=15.9 Hz, 1H); $^{13}$C NMR (CDCl$_3$) δ 200.1, 170.6, 139.6, 137.9, 132.7, 131.3, 130.7, 130.2, 128.7, 128.6, 128.5, 127.3, 126.3, 126.0, 125.8, 125.0, 124.9, 124.6, 124.0, 122.5, 122.4, 73.9, 62.4, 57.0, 49.9, 45.0, 39.1, 38.1, 37.0, 36.6, 31.9, 31.8, 27.8, 24.7, 22.8, 21.5, 21.1, 19.3, 13.5 (only 39 of the expected 40 resonances are observed); MS (CI, NH$_3$) m/z 571 (100, [M+H]$^+$).

Synthesis of 3β-acetoxy-pregn-5-ene-21-(1-methylpyrenyl)-20-one (compound 3)

4.2 mL of a 1M solution of TiCl$_4$ in $CH_2Cl_2$ is added to an ice-cooled solution of compound 2 (1 g, 1.75 mmol) in 20 mL of $CH_2Cl_2$ and the resulting dark brown solution is stirred for 10 min. Et$_3$SiH (419 μL, 2.63 mmol) is added in one go and the solution is heated at ambient temperature and stirred for 45 min. The solution is poured into a saturated solution of NaHCO$_3$ and the organic products are extracted with $CH_2Cl_2$ (3×80 mL) The combined extracts are dried over sodium sulphate, concentrated under reduced pressure and after column chromatography ($CH_2Cl_2$/AcOEt 98:2) produce 601 mg (60%) of compound 3 in the form of a pale yellow solid; mp 91° C.; TLC ($CH_2Cl_2$/AcOEt 98:2) $R_f$ 0.9; IR (KBr, cm$^{-1}$) 2938s, 2902s, 1729s, 1701s, 1456w, 1436w, 1362m, 1246s, 1095w, 1031m, 906w, 845m, 731m; $^1$H NMR (CDCl$_3$) δ 0.49 (s, 3H), 0.86 (s, 3H), 1.94 (s, 3H), 0.6-2.4 (m, 20H), 2.77 (t, J=8.1 Hz, 2H), 3.51 (t, J=7.5 Hz, 2H), 4.49 (m, 1H), 5.23 (d, J=4.2 Hz, 1H), 7.76-8.14 (m, 9H); $^{13}$C NMR (CDCl$_3$) δ 210.5, 170.5, 139.6, 135.6, 131.4, 130.9, 130.0, 128.5, 127.6, 127.5, 127.3, 126.7, 125.9, 125.1, 125.0, 124.9, 124.8, 123.0, 122.3, 73.8, 63.1, 56.7, 49.7, 46.1, 44.2, 38.8, 38.1, 36.9, 36.5, 31.7, 31.6, 27.7, 27.4, 24.5, 23.0, 21.4, 20.9, 19.2, 13.4 (only 39 of the expected 40 resonances are observed); MS (CI, NH$_3$) m/z 590 (100, [M+NH$_4$]$^+$), 573 (98, [M+H]$^+$).

Synthesis of 3β-hydroxy-pregn-5-ene-21-(1-methylpyrenyl)-20-one (compound 4).

5 mL of dry methanol and 5 mL of a solution at 30% by weight of sodium methanolate in methanol are added successively to a solution of compound 3 (600 mg, 1 mmol) in 10 mL of $CH_2Cl_2$ and the solution is stirred for 4 h at ambient temperature. 200 mL water is added and the organic products are extracted with $CH_2Cl_2$ (3×100 mL). The combined organic extracts are rinsed with salt water, dried over sodium sulphate, filtered, and evaporated. Purification by flash chromatography on silica G60 (0.040-0.063 mm), elution with $CH_2Cl_2$ in AcOEt (85/15) produce 302 mg (95%) of compound 4 in the form of an off-white solid; mp 199° C.; TLC ($CH_2Cl_2$/AcOEt 85:15) $R_f$ 0.5; IR (KBr, cm$^{-1}$) 3428m, 2930s, 1700s, 1458w, 1436w, 1357w, 1108w, 1054m, 845s, 755s; $^1$H NMR (CDCl$_3$) δ 0.55 (s, 3H), 0.89 (s, 3H), 0.70-2.24 (m, 19H), 2.40 (t, J=9 Hz, 1H), 2.84 (t, J=6 Hz, 2H), 3.42 (m, 1H) 3.55 (t, J=9 Hz, 2H), 5.24 (d, J=4.8 Hz, 1H), 7.80-8.18 (m, 9H); $^{13}$C NMR (CDCl$_3$) δ 210.5, 140.7, 135.7, 131.4, 130.9, 130.0, 128.5, 127.6, 127.5, 127.3, 126.8, 125.9, 125.1, 125.0, 124.9, 124.8, 123.0, 121.4, 71.7, 63.2, 56.9, 49.9, 46.1, 44.3, 42.2, 38.9, 37.2, 36.5, 31.8, 31.7, 31.6, 27.4, 24.5, 23.0, 21.0, 19.3, 13.5 (only 37 of the expected 38 resonances are observed); MS (CI, NH$_3$) m/z 548 (100, [M+NH$_4$]$^+$), 531 (17, [M+H]$^+$).

Synthesis of 3β-tert-butyldimethylsilyloxy-pregn-5-ene-21-(1-methylpyrenyl)-20-one (compound 5).

A solution of tert-butyldimethylsilyl chloride (68 mg, 452 mmol) in 2 mL of CH$_2$Cl$_2$ is added, using a syringe, to a solution of compound 4 (200 mg, 377 μmol) and imidazole (51 mg, 754 mmol) in 5 mL of CH$_2$Cl$_2$. After stirring for 12 h at ambient temperature, 50 mL water is added and the organic products are extracted with dichloromethane (3×50 mL). The combined organic extracts are rinsed with salt water, dried over sodium sulphate, filtered, and evaporated. Purification by flash chromatography on silica G60 (0.040-0.063 mm), elution with dichloromethane produce 231 mg (95%) of compound 5 in the form of an off-white solid; mp 100° C.; TLC (CH$_2$Cl$_2$) R$_f$ 0.9; IR (KBr, cm$^{-1}$) 2929s, 2852s, 1703s, 1461m, 1381m, 1359m, 1250m, 1183w, 1091s, 843s, 773m; $^1$H NMR (CDCl$_3$) δ 0.00 (s, 6H), 0.47 (s, 3H), 0.60-2.22 (m, 32H), 2.72 (t, J=7.5 Hz, 2H), 3.39 (m, 1H) 3.49 (t, J=7.8 Hz, 2H), 5.17 (d, J=3.9 Hz, 1H), 7.73-8.12 (m, 9H); $^{13}$C NMR (CDCl$_3$) δ 210.4, 141.4, 135.7, 131.4, 130.9, 130.0, 128.5, 127.6, 127.5, 127.3, 126.8, 125.9, 125.1, 125.0, 124.9, 124.8, 123.1, 120.9, 72.6, 63.0, 56.7, 49.9, 46.0, 44.2, 42.8, 38.8, 37.3, 36.5, 32.1, 31.8, 31.7, 27.4, 26.2, 26.0, 25.8, 24.5, 23.0, 21.0, 19.4, 18.3, 13.4, −4.5 (only 42 of the expected 44 resonances are observed); MS (CI, CH$_4$) m/z 645 (100, [M +H]$^+$).

Synthesis of 3β-tert-butyldimethylsilyloxy-pregn-5-ene-21-(t-methylpyrenyl)-20-methylidene (compound 6).

48 mg of NaH (2 mmol) is added to 3 mL of dry DMSO and the suspension is stirred and heated at 65° C. until all the sodium hydride is dissolved. The solution is cooled down to ambient temperature and methyl-triphenylphosphonium bromide (715 mg, 2 mmol) is added by portions over 5 min. The reaction is slightly exothermic and the solution is stirred for an additional duration of 45 min. This solution is added in one go to a solution of compound 5 (645 mg, 1 mmol) in 5 mL of THF and the resulting solution is stirred and heated at 70° C. for 12 h. After cooling down, 50 mL of water is added and the organic products are extracted with dichloromethane (3×50 mL). The combined organic extracts are rinsed with salt water, dried over sodium sulphate, filtered, and evaporated. Purification by flash chromatography on silica G60 (0.040-0.063 mm), elution with pentane in CH$_2$Cl$_2$ (75/25) produce 514 mg (80%) of compound 6 in the form of an off-white solid; mp 63° C.; TLC (pentane/CH$_2$Cl$_2$ 75:25) R$_f$ 0.85; IR (KBr, cm$^{-1}$) 2928s, 2851s, 1636w, 1460m, 1434m, 1380w, 1249m, 1088s, 888m, 842s, 773m; $^1$H NMR (CDCl$_3$) δ 0.00 (s, 6H), 0.54 (s, 3H), 0.83 (s, 9H), 0.91 (s, 3H), 0.75-2.30 (m, 32H), 2.47 (m, 2H), 3.40 (m, 3H), 4.85 (s, 1H), 5.01 (s, 1H), 5.24 (d, J=6.0 Hz, 1H), 7.77-8.20 (m, 9H); $^{13}$C NMR (CDCl$_3$) δ 149.1, 141.6, 136.8, 133.9, 133.6, 131.5, 131.0, 129.8, 128.7, 128.6, 128.5, 128.4, 127.6, 127.3, 127.2, 126.6, 125.6, 125.1, 124.9, 124.7, 123.4, 121.1, 110.1, 72.7, 56.7, 56.3, 50.3, 43.3, 42.9, 39.9, 38.8, 37.4, 36.7, 32.9, 32.3, 32.1, 31.9, 26.0, 24.3, 21.2, 19.5, 18.3, 12.9, −4.5 (only 44 of the expected 45 resonances are observed); MS (CI, NH$_3$) m/z 660 (10, [M+NH$_4$]$^+$), 511 (100).

Synthesis of 3β-hydroxy-pregn-5-ene-21-(1-methylpyrenyl)-20-methylidene (compound 7).

2.5 mL of TBAF (1M) in THF is added to a solution of compound 6 (300 mg, 466 μmol) in 5 mL of dry THF and the solution is stirred and heated at 65° C. for 12 h. After cooling down, 100 mL of water is added and the organic products are extracted with dichloromethane (3×50 mL). The combined organic extracts are rinsed with salt water, dried over sodium sulphate, filtered, and evaporated. Purification by flash chromatography on silica G60 (0.040-0.063 mm), elution with CH$_2$Cl$_2$ in AcOEt (98/2) produce 209 mg (85%) of compound 7 in the form of an off-white solid; mp 84° C.; TLC (CH$_2$Cl$_2$/AcOEt 98:2) R$_f$ 0.4; IR (KBr, cm$^{-1}$) 3364m, 2929s, 1636w, 1458w, 1434w, 1375w, 1182w, 1056m, 888m, 843s, 712w; $^1$H NMR (CDCl$_3$) δ 0.52 (s, 3H), 0.65-2.25 (m, 32H), 2.3-2.6 (m, H), 3.27-3.44 (m, H), 4.83 (s, 1H), 4.99 (s, 1H), 5.24 (d, J=4.5 Hz, 1H), 7.75-8.18 (m, 9H); $^{13}$C NMR (CDCl$_3$) δ 149.1, 140.8, 136.8, 131.5, 130.9, 129.8, 128.6, 127.5, 127.3, 127.2, 126.6, 125.8, 125.1, 124.9, 124.7, 123.4, 121.6, 110.1, 71.8, 56.6, 56.3, 50.2, 43.2, 42.3, 39.9, 38.8, 37.3, 36.6, 32.9, 32.3, 31.8, 31.7, 29.7, 26.0, 24.3, 21.1, 19.4, 12.9 (only 38 of the expected 39 resonances are observed); MS (CI, NH$_3$) m/z 546 (38, [M+NH$_4$]$^+$), 529 (89, [M+H]$^+$), 217 (100)

Loading the methyl-β-cyclodextrins with the Pyrene cholesterol (4) or (7).

3 ml of an aqueous solution of methyl-β-cyclodextrins at 75 mM is heated to a temperature of 75° C., 20 μl of a saturated solution of Pyrene cholesterol (4) or (7) dissolved to saturation in DMF (~187.5 mM i.e. 1 mg/10 μl of DMF) is added progressively. The reaction medium is left under stirring for 30 mn at 75° C. then left to cool. The solution is filtered through a 0.22 μm filter and can be kept at 4° C. for several days. It corresponds to 1 Pyrene cholesterol (4) or (7) for 60 molecules of methyl-β-cyclodextrins.

Cell Marking

Confluence cells immobilised on a 22 by 22 mm silica slice are placed in a 35 mm diameter Petri dish and covered by 1.2 ml of a 0.22 μm-filtered solution and composed of 15 ml of base medium (DMEM with 1% foetal calf serum) plus 1 ml solution of methyl-β-cyclodextrins loaded with Pyrene cholesterol (4) or (7). The mixture is left to incubate at 37° C. for between 1 and 15 mn according to the desired marking rate. Then the medium is replaced 4 times with 1.2 ml of PBS Ca++Mg++.

The measurements are carried out either on these preparations or after having replaced the PBS with DMEM.

The images are produced with a Zeiss axioplanII microscope using a 63× oil-immersion objective (Plan-Neofluoar, NA=1.4) and a CCD camera (C2400-75i Hamamatsu) equipped with the Argus 20 system (Hamamatsu) which removes the background noise directly on the preparation corresponding to the following mounting: after the slice carrying the marked cells has been turned upside-down on a slide provided with cross-pieces, a chamber the volume of which is close to 120 μl is thus produced and filled with DMEM medium. The two ends of the mounting are sealed by gluing onto the cross-pieces, the two other sides remain open in order to allow extrinsic additives: ligands etc to be introduced.

The fluorescence spectra are produced on these mountings on an AMINCO 500 spectrofluorimeter. The excitation wavelength is 335 nm bp 5 nm, the emission spectrum being recorded after 370 nm bp 4 nm and with a resolution of 0.25 nm per point.

Figure 1:
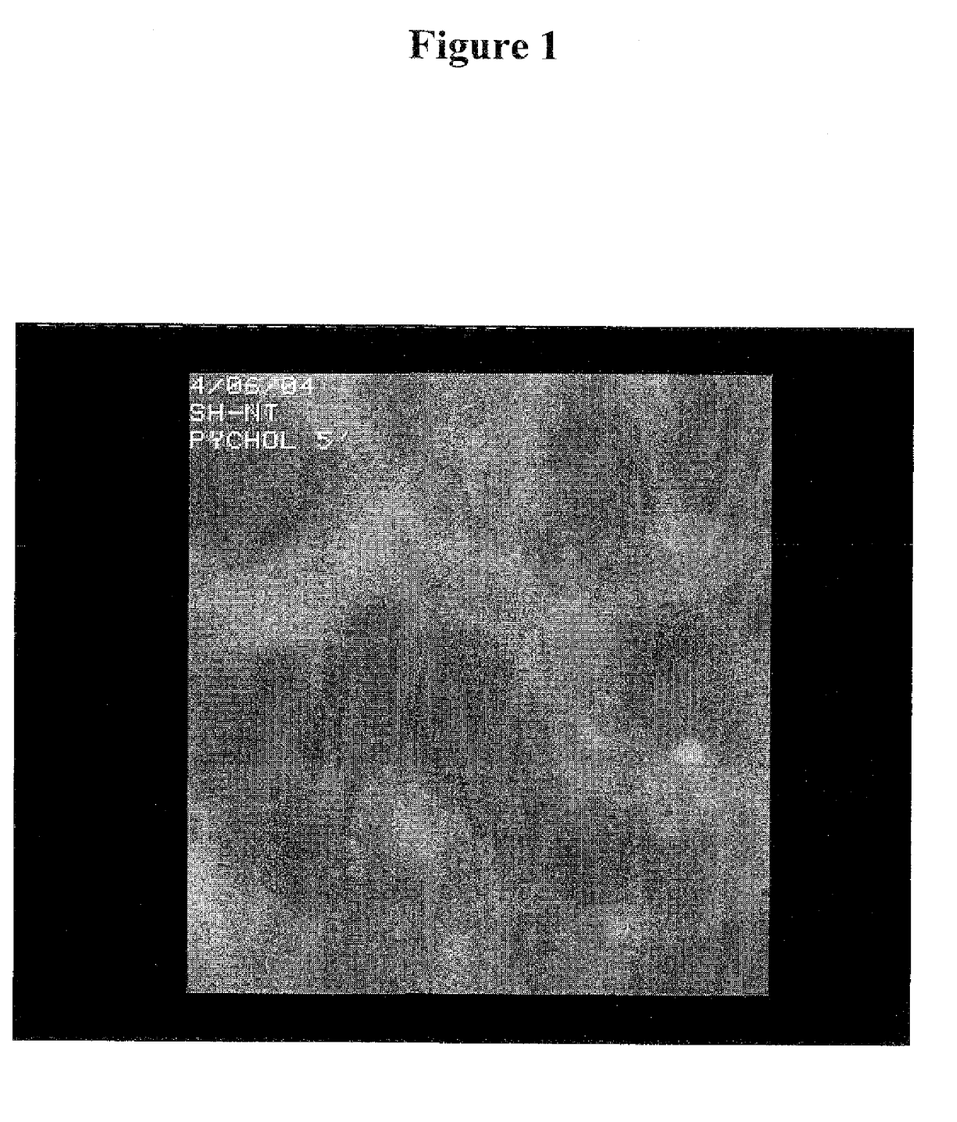
FIG. 1 represents the marking of SH-SY5Y cell membranes in vivo using methyl-β-cyclodextrins loaded in a pyrene-ketone-cholesterol probe. The insertion can be done at greater than 40% and is a function of the marking time.
Figure 2:
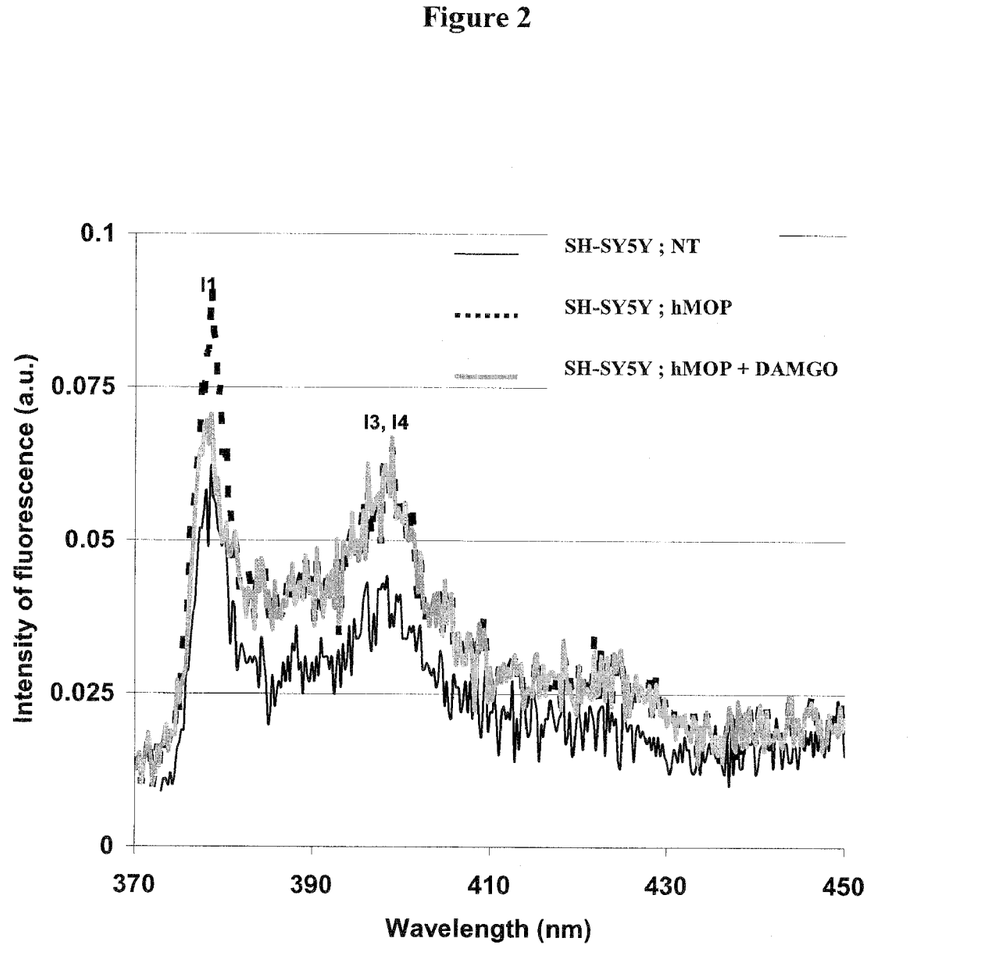
FIG. 2 represents the fluorescence spectra carried out on cells SH-SY5Y immobilised on solid support (silica slice) after incorporation in the plasma membrane, using methyl-β-cyclodextrin, the pyrene-ketone-cholesterol probe of formula (4). Shown in the black continuous line, the cells not transfected by the GPCR μ with opioids (hMOP); in the thick dotted line, the cells transfected by the latter; in the thick grey continuous line, the previous sample to which the DAMGO agonist was added under saturation conditions.

Result of the Measurements of the Fluorescence Spectra on Neuroblastoma SH-SV5Y Overexpressing or Not Expressing hMOP and With or Without Pyene-Ketone-Cholesterol of Formula (4) (FIG. 2)

By comparing the spectra in black dotted lines and continuous grey lines which correspond to the same cell lawn of SH-SY5Y cells overexpressing hMOP, it is noted that after the addition of the DAMGO agonist, while the spectra at the level of bands I3 and I4 are unchanged, the bands I1 have different intensities. This indicates, as a result of the reduction of the spectrum represented in grey, a reduction in the membrane polarity after the addition of DAMGO. It corresponds to an increase in the quantity of phase lo (i.e. an increase in the average thickness of membrane ) induced by the receptor following the addition of DAMGO.

REFERENCES

[1] Simons, K., and D. Toomre (2000). *Nat. Rev. Mol. Cell Biol.* 1:31-39.
[2] London, E., and D. A. Brown (2000). *Biochim. Biophys. Acta* 1508:182-195.
[3] Giacondi, M. C., V. Vie, E. Lesniewska, J. P. Goudonnet, and C. Le Grimellec (2000). *J. Struct. Biol.* 131:38-43.
[4] Simons, K., and E. Ikonen (1997). *Nature* 387:569-572.
[5] Ipsen, J. H., G. Karlstrom, O. G. Mouritsen, H. Wennerstrom, M. J. Zuckermann (1987). *Biochim. Biophys. Acta* 905:162-172.
[6] Sankaram, M. B. and T. E. Thompson (1990). *Biochemistry.* 29:10676-84.
[7] Vist, M. R., J. H. Davis (1990). *Biochemistry.* 29:451-464.
[8] McMullen, T. P., McElhaney (1995). *Biochim. Biophys. Acta.* 1234:90-98.
[9] Srivastava, M., H. Ow, D. Larson, D. Holowka, U. Wiesner, W. Webb, B; Baird (2002). *Biophys. J.* 82:498a.
[10] Jacobson, K., C. Dietrich (1999). *Trends Cell Biol.* 9:87-91.
[11] Salamon Z, E. Varga, G. Tollin (1994). *Biochemistry* 33:13706.
[12] Salamon, Z., S. Cowell, E. Varga, H. I. Yamamura, V. J. Hruby, G. Tollin (2000). *Biophys. J.* 79:2463-2474.
[13] Dumas F., M. M. Sperotto, M. C. Lebrun, J. F. Tocanne, O. G. Mouritsen (1997). *Biophys. J.* 73:1940-1953.
[14] Dumas F., M. C. Lebrun, J. F. Tocanne (1999). *FEBS Lett.* 458:271-277.
[15] Lagane B., G. Gaibelet, E. Meilhoc, J M Masson, L. Cezanne, A. Lopez *J. Biol. Chem.* (2000). 327:33197-33200
[16] "De la distribution laterale du cholesterol dans les membranes biologiques à son rôle dans le contrôle de l'activité des protéines membranaires-cas du RCPGμ". B. Lagane, Thèse de l'Université P. Sabatier. Toulouse, November 2001.
[17] Lagane B., S. Mazères, C. Le Grimellec, L. Cézanne, A Lopez, *Biophys. Chem.* (2002). 95 :7-22.
[18] L'Heureux, G P., M. Fragata (1987). *J. Coll. Int. Scien.* 117:513-521.
[19] Mazères, S., B. Lagane, M. Welby, V. Trégou, A. Lopez (2001). *Spectrochim. Acta* A57:2297-2311.
[20] Mazères S., F. Rodriguez, J. F. Tocanne et A. Lopez (1996). *Analusis* 24:M20-M22.
[21] Daumas F., N. Destainville, C. Millot, A. Lopez, D. Dean, L. Salomé (2003). *Biophys. J.* 84:356-366
[22] Salomé L., F. Daumas, N. Destainville, C. Millot, A. Lopez, D. Dean (2002). *Biophys. J.* 82:40a
[23] Daumas F., M. Corbani, S. Ducasse, C. Millot, A. Lopez, L. Salomé (2002). *Biophys. J.* 82:216a
[24] Salomé L., J- L Cazeil, A Lopez, J F Tocanne (1998). *Eur Biophys J.* 27:391-402
[25] Cézanne L., S. Lecat, B. Lagane, C. Millot, J Y.Vollmer, H. Matthes, J L.Galzi, A. Lopez (2004). *J. Biol Chem.* 279:45057-45067.
[26] Ohtani, Y., T. Irie, K. Uekama, K. Fukunaga, and J. Pitha (1989) *Eur J Biochem.* 186:17-22.

The invention claimed is:
1. A pyrene cholesterol compound of general formula (I):

wherein X represents a $CH_2$ group or an oxygen atom and n is an integer from 2 to 10.

2. The pyrene-cholesterol compound according to claim 1, said pyrene-cholesterol compound is pyrene-ketone-cholesterol of following formula (4):

3. The pyrene-cholesterol compound according to claim 1, said pyrene-cholesterol compound is pyrene-methylene-cholesterol of following formula (7):

4. The pyrene-cholesterol compound according to claim 1, wherein n is an integer from 2 to 6.

5. A composition comprising at least one pyrene cholesterol compound according to claim 1, in a mixture with a transporter intended to exchange cholesterol or a phospholipid, naturally present in said cell membranes with said at least one pyrene-cholesterol compound.

6. The composition according to claim 5, wherein the transporter is selected from the group consisting of a methyl-β-cyclodextrin, a α-cyclodextrin, a β-cyclodextrin, and a γ-cyclodextrin.

7. A method for synthesizing the compounds of formula (I) according to claim 1, comprising the steps of:

a) reacting the pregnenolone of formula (a) and the pyrene derivative of formula (b) wherein n is an integer from 2 to 10, in the presence of EtOK, EtOH, in CH$_2$Cl$_2$ at a temperature between 5° C. and 20° C. and for a duration comprised between 10 and 72 hours, which produces the following compound of formula (1):

(a)

+

(b)

(1)

b) reacting the compound of formula (1) obtained in the previous stage in the presence of 1.5 equivalents of Ac$_2$O, 10 mol % of DMAP, 1 equivalent of Et$_3$N, in CH$_2$Cl$_2$ for 3 hours, which produces the following compound of formula (2):

(1)

(2)

c) reacting the compound of formula (2) obtained in the previous stage in the presence of 2 equivalents of TiCl$_4$, 1.5 equivalents of Et$_3$SiH, in CH$_2$Cl$_2$ for 45 minutes at ambient temperature, which produces the following compound of formula (3):

d) reacting the compound of formula (3) obtained in the previous stage in the presence of MeONa, in CH$_2$Cl$_2$ for 4 hours at ambient temperature, leads to the following compound of formula (4):

(4)

e) reacting the compound of formula (4) obtained in the previous stage in the presence of TBDMSCl, imidazole, $CH_2Cl_2$ for 12 hours at ambient temperature, which produces the following compound of formula (5):

f) reacting the compound of formula (5) obtained in the previous stage in the presence of 2 equivalents of $CH_2=PPh_3$, in a THF/DMSO mixture, for 12 hours at 75° C., which produces the following compound of formula (6):

g) reacting the compound of formula (6) obtained in the previous stage in the presence of 5 equivalents of TBAF, in THF, for 12 hours at 65° C., produces the following compound of formula (7):

8. The method according to claim 7, wherein n is an integer from 2 to 6 the pyrene derivative of formula (b).

9. A method for detecting and measuring effects of external stimuli selected from the group consisting of temperature, pressure and modulation by an extrinsic agent of a lipid concentration initially contained in cell membranes from compounds of the cyclodextrin family in the presence of at least one pyrene-cholesterol compound defined in claim 1, said method comprising:
incorporating said at least one pyrene-cholesterol compound into said cell membranes;
applying external stimuli to said cell membranes, said external stimuli being selected from the group consisting of temperature, pressure, and modulation by an extrinsic agent of the lipid concentration initially contained in said cell membranes, and combinations thereof, said extrinsic agent being compounds of the cyclodextrin family in the presence of said at least one pyrene-cholesterol compound;
applying to said cell membranes radiation of wavelength $\lambda_{ex}$ being comprised between 330 nm and 350 nm, said $\lambda_{ex}$ being characteristic of the absorption of pyrene;
measuring fluorescence radiation intensity emitted by said cell membranes at emission wavelengths of 375 to 385 nm, which are characteristic of pyrene emission band 1, said intensity being a function of the polarity of the membrane;
measuring fluorescence radiation intensity of at least one of two fluorescence radiations emitted by said cell membranes at emission wavelengths of between 390 nm and 425 nm, which are characteristic of pyrene emission bands 3 and 4, said intensity being a function of the quantity of pyrene-cholesterol compounds, in said cell membranes;
determining a ratio of the intensity of band 1 to that of band 3 or 4, said ratio being $I_1/I_3$ or $I_1/I_4$;
correlating said ratio and the polarity of said cell membranes to provide the functional organization of said cell membranes in the presence or absence of external stimuli.

10. The method according to claim 9, further comprising:
measuring polarity or permeability of said cell membranes, the concentration of one or more constituents of said cell membranes, and spatial and collective organization of the constituents of said cell membranes.

11. The method according to claim 9, said method further comprising:
screening bioactive products capable of being agonists or antagonists of receptors present in said cell membranes or on the surface of said cell membranes, said bioactive products capable of being used for the preparation of medicaments intended for the treatment of pathologies involving said receptors; and
carrying out in vitro diagnosis of pathologies from cells of patients using given products used as markers of these pathologies, or
monitoring the orientation of the therapeutic indication of a medicament comprising a bioactive product as defined above, by determination in vitro of the agonist or antagonist effect of this medicament on the cells of the patient capable of being treated with this medicament.

12. The method according to claim 9, wherein said cell membranes are selected from the group consisting of extracted cell membranes and cell membranes of living cells.

13. The method according to claim 9, wherein said cell membranes are eukaryotic cells selected from the group consisting of: CHO, HEK, NRK, AEB, AEH, SHYSY, 3T3, primary cultures of neurones, and fibroblasts.

14. The method according to claim 9, said method further comprising:
- screening bioactive products capable of being agonists or antagonists of receptors present in cell membranes or partially inserted into said cell membranes, said bioactive products being capable of use for preparing medicaments for treating pathologies in which said receptors are involved, or
- monitoring the direction of the therapeutic indication of a medicament comprising a bioactive product as defined above, by in vitro determination of the agonist or antagonist effect of this medicament on the cells of the patient capable of being treated with this medicament, and further comprising:
- placing said cell membranes into which said at least one pyrene-cholesterol compound has been inserted in the presence of a bioactive product, or a bank of bioactive products, under conditions allowing said bioactive products to bond with receptors of said cell membranes,
- rinsing said cell membranes to remove any bioactive product which is not capable of bonding with a membrane receptor prior to applying to said cell membrane of wavelength $\lambda_{ex}$,
- comparing the ratios $I_1/I_3$ or $I_1/I_4$ to ratios $I'_1/I'_3$ or $I'_1/I'_4$, measured in the absence of bioactive products, which allows the agonist or antagonist or inverse antagonist nature of the bioactive products tested to be determined, an agonist product being characterized by a ratio $I_1/I_3$ or $I_1/I_4$ respectively greater than or less than the ratio $I'_1/I'_3$ or $I'_1/I'_4$ according to the type of said membrane receptors, an antagonist product being characterized by a ratio $I_1/I_3$ or $I_1/I_4$ equivalent respectively to the ratio $I'_1/I'_3$ or $I'_1/I'_4$, an inverse antagonist product being characterized by an inverse effect to that of an agonist product such that a ratio $I_1/I_3$ or $I_1/I_4$ is respectively less than or greater than the ratio $I'_1/I'_3$ or $I'_1/I'_4$.

15. The method according to claim 9, wherein said cell membranes are eukaryotic cell membranes, and said method is carried out in vitro on eukaryotic cells, and comprises a stage of incorporation of said at least one pyrene-cholesterol compound into said eukaryotic cell membranes.

16. The method according to claim 9, wherein incorporating said at least one pyrene-cholesterol compound into said cell membranes is carried out using a transporter intended to exchange cholesterol, a phospholipid, naturally present in said cell membranes, with said at least one pyrene-cholesterol compound.

17. The method according to claim 16, wherein the transporter is selected from the group consisting of a methyl-$\beta$-cyclodextrin, a $\alpha$-cyclodextrin, a $\beta$-cyclodextrin, and a $\gamma$-cyclodextrin.

18. The method according to claim 9, wherein said at least one pyrene-cholesterol compound is incorporated into said cell membranes in a proportion of about 0.1 to 2% of the surface concentration of lipids present in said cell membrane.

19. The method according to claim 10, wherein incorporating said at least one pyrene-cholesterol compound into said cell membranes is realized through the incorporation of a composition comprising said at least one pyrene-cholesterol compound in a mixture with a transporter intended to exchange cholesterol or a phospholipid, naturally present in said cell membranes with said at least one pyrene-cholesterol compound or said combination.

* * * * *